(12) United States Patent
Du Plessis

(10) Patent No.: US 11,780,886 B2
(45) Date of Patent: Oct. 10, 2023

(54) MODIFIED VIRAL VECTORS AND METHODS OF MAKING AND USING THE SAME

(71) Applicant: uniQure IP B.V., Amsterdam (NL)

(72) Inventor: David Johannes Francois Du Plessis, Amsterdam (NL)

(73) Assignee: uniQure IP B.V., Amsterdam (NL)

( * ) Notice: Subject to any disclaimer, the term of this patent is extended or adjusted under 35 U.S.C. 154(b) by 494 days.

(21) Appl. No.: 16/911,171

(22) Filed: Jun. 24, 2020

(65) Prior Publication Data

US 2020/0325181 A1    Oct. 15, 2020

Related U.S. Application Data

(63) Continuation of application No. PCT/EP2018/097091, filed on Dec. 28, 2018.

(30) Foreign Application Priority Data

Dec. 29, 2017    (EP) .................................... 17211221

(51) Int. Cl.
| | | |
|---|---|---|
| *C07K 14/005* | (2006.01) | |
| *A61K 35/76* | (2015.01) | |
| *C12N 7/00* | (2006.01) | |
| *C12N 15/86* | (2006.01) | |

(52) U.S. Cl.
CPC ............ *C07K 14/005* (2013.01); *A61K 35/76* (2013.01); *C12N 7/00* (2013.01); *C12N 15/86* (2013.01); *C12N 2720/00043* (2013.01); *C12N 2750/14122* (2013.01)

(58) Field of Classification Search
CPC .......... C12N 15/86; C12N 2750/14123; C12N 15/87; C12N 2750/00023; C12N 2750/00031; C12N 2750/14311; C12N 2750/14143; C12N 7/00; C12N 2750/00034; C12N 2750/14011; C12N 2750/14022; C12N 2750/14021; C12N 2750/14023; C12N 2750/14031; C12N 2750/14041; C12N 2750/14034; C12N 2750/14033; C12N 2750/14032; C12N 2750/14111; C12N 2750/14121; C12N 2750/14122; C12N 2750/14141; C12N 2750/14134; C12N 2750/14133; C12N 2750/14132; C12N 2750/14131; A61K 35/76

See application file for complete search history.

(56) References Cited

U.S. PATENT DOCUMENTS

| | | |
|---|---|---|
| 2003/0148506 A1 | 8/2003 | Kotin et al. |
| 2004/0197895 A1 | 10/2004 | Kotin et al. |

FOREIGN PATENT DOCUMENTS

| | | |
|---|---|---|
| WO | WO-2005/072364 A2 | 8/2005 |
| WO | WO-2007/046703 A | 4/2007 |

OTHER PUBLICATIONS

Bennett A et al: "Thermal Stability as a Determinant of AAV Serotype Identity", Molecular Therapy—Methods & Clinical Develop, vol. 6, Sep. 1, 2017 (Sep. 1, 2017), pp. 171-182, XP055478004, ISSN: 2329-0501, DOI: 10.1016/j.omtm.2017.07.003.

Grieger J C et al: "Packaging Capacity of Adeno-Associated Virus Serotypes: Impact of Larger Genomes on Infectivity and Postentry Steps", Journal of Virology, The American Society for Microbiology, US, vol. 79, No. 15, Aug. 1, 2005 (Aug. 1, 2005), pp. 9933-9944, XP009054356, ISSN: 0022-538X, DOI:10.1128/JVI.79.15.9933-9944.

International Search Report received in International Application No. PCT/EP2018/097091 dated Feb. 25, 2019, 3 pages.

Ruffing M et al: "Assembly of Viruslike Particles by Recombinant Structural Proteins of Adeno-Associated Virus Type 2 In Insect Cells", Journal of Virology, The American Society for Microbiology, US, vol. 66, No. 12, Dec. 1, 1992 (Dec. 1, 1992), pp. 6922-6930, XP001032438, ISSN: 0022-538X. abstract.

Warrington K H et al: "Adeno-Associated Virus Type 2 VP2 Capsid Protein is Nonessential and Can Tolerate Large Peptide Insertions at Its N Terminus", Journal of Virology, The American Society for Microbiology, US, vol. 78, No. 12, Jun. 1, 2004 (Jun. 1, 2004).

*Primary Examiner* — Bao Q Li
(74) *Attorney, Agent, or Firm* — FOLEY & LARDNER LLP; Sunit Talapatra

(57) ABSTRACT

The present invention relates to production of parvoviral vectors to produce adeno-associated virus (AAV) for gene therapy. In particular the invention relates to improvements in parvoviral vectors that increase the packaging capacity, production efficiency, and infectivity of AAV virions that is necessary for large scale manufacturing of AAV for clinical purposes.

12 Claims, 4 Drawing Sheets

MODIFIED VIRAL VECTORS AND METHODS OF MAKING AND USING THE SAME

CROSS-REFERENCE TO RELATED APPLICATIONS

This application is a continuation of International Application No. PCT/EP2018/097091, filed Dec. 28, 2018, which claims the benefit of and priority to European Application No. 17211221.1, filed Dec. 29, 2017, both of which are incorporated by reference herein in their entireties.

The present disclosure generally relates to the field of producing parvoviral vectors for delivering nucleic acids into foreign hosts and gene therapy. More specifically, the disclosure relates to improvements in large scale production of parvoviral particles in insect cells.

BACKGROUND

Adeno-associated virus (AAV) may be considered as one of the most promising viral vectors for human gene therapy. AAV has the ability to efficiently infect dividing and non-dividing human cells, the AAV viral genome integrates into a single chromosomal site in the host cell's genome, and most importantly, even though AAV is present in many humans it has never been associated with any disease. In view of these advantages, recombinant adeno-associated virus (rAAV) therapies are being evaluated in clinical trials for hemophilia B, malignant melanoma, cystic fibrosis, and other diseases. Numerous clinical trials and approval of gene therapy medicines, such as Alipogene tiparvovec (Glybera®, uniQure), and recently Voretigene neparvovec-rzyl (Luxturna® Spark Therapeutics), suggest that AAV will become main stay of clinical practice.

Despite the promise of AAV gene therapy, two limitations on clinical application of AAV have been identified. First, achieving large scale consistent production of infective AAV particles is difficult. Second, the small capsid size of AAV is a major limitation on clinical application of human diseases associated with large genes, such as hemophilia A and cystic fibrosis.

Scaling up production of AAV for gene therapy is not trivial, and it is imperative that the large scale AAV meet the strict requirements for manufacturing and clinical practice. In general, there are two main types of production systems for recombinant AAV. On the one hand there are conventional production systems in mammalian cell types (such as 293 cells, COS cells, HeLa cells, KB cells) and on the other hand production systems using insect cells.

The mammalian production system suffers from several drawbacks, which may include the limited number of rAAV particles generated per cell and cumbersome large scale manufacturing. See generally Clark et al., Kidney Int. 61: 9-15 (2002). For a clinical study, more than $10^{15}$ particles of rAAV may be required. Producing this number of rAAV particles requires transfection and culture of approximately $10^{11}$ cultured human 293 cells, the equivalent of 5,000 175-cm² flasks of cells. This makes preparation for a clinical trial laborious and impractical, and it suggests that the scale up required for commercialization using a mammalian culture would be virtually infeasible. Furthermore, there is always a risk that a vector produced in a mammalian culture could be contaminated with undesirable, perhaps pathogenic, material present in the mammalian host cell.

Production of rAAV in insect cells is an alternative that addresses many of the limitations of mammalian culture. See, e.g. Urabe et al., Hum. Gene Ther. 13: 1935-1943 (2002); US 20030148506, and US 20040197895. However, producing AAV in insect cells has been difficult to scale up as well, at least in part due to the instability of the viral vectors used for expression in insect systems. See Kohlbrenner et al. Mol. Ther. 12:1217-25 (2005); WO2005/072364). While attempts have been made to improve stability (e.g., by expressing Rep52 and Rep78 from two separate viral vectors) sustained rAAV production over multiple culturing passages has remained difficult. Moreover, the rAAV produced within these cultures may be less or not infectious (see, e.g., Kohlbrenner et al. ((2005, supra)), thus limiting the therapeutic utility of some rAAV produced in insect cells.

Improving commercial scale production of AAV has been further limited by an incomplete understanding of the specific roles of the capsid protein VP1, VP2, and VP3 in AAV assembly and infectivity. Muzyczka et al., Chapter 69: Parvoviridae: The viruses and their replication in FIELDS VIROLOGY (4th ed., 2001). Wild-type AAV capsids consist of a combination of roughly 60 total capsid VP1, VP2 and VP3 proteins in a stoichiometric ratio of about 1:1:10, respectively. Conventionally, it was believed that the stoichiometry of the capsid proteins was important to achieve good potency and transduction efficiency. Indeed, the art has often focused on trying to maintain the precise, naturally-occurring ratio of capsid proteins when producing rAAV in insect cells. See Urabe et al. (2002, supra); WO2007/046703 and. While attempts have been made to alter the make-up of rAAV expressed in insect cells, these attempts have suggested that VP2 is required for capsid formation in insect cells. Ruffing et al., J. Virol., 66 (12): 6922-30 (1992); Grieger et al., J. Virol., 79 (15): 9933-44 (2005).

Therefore, there remains a need in the art for improvements in rAAV production that will allow for efficient commercial scale up of therapeutically useful rAAV. The present disclosure satisfies these needs.

SUMMARY

Described herein are recombinant adeno-associated viruses (rAAV) that lack a VP2 capsid ("VP2-less") and are produced in insect cells, as well as methods of making and using the same. These VP2-less rAAV can be efficiently scaled up for commercial production, have an increased payload capacity compared to rAAV that comprise a VP2 capsid protein, and maintain infectivity, which makes them suitable for therapeutic purposes.

In one aspect, the present disclosure provides insect cells that express AAV VP1 protein and AAV VP3 protein, but do not express AAV VP2 protein.

In some embodiments, the insect cells may comprise a single nucleotide sequence encoding AAV VP1 protein and AAV VP3 protein, while in some embodiments, the insect cells may comprise a first nucleotide sequence encoding AAV VP1 protein and a separate, second nucleotide sequence encoding AAV VP3 protein. For example, when both VP1 and VP3 are encoded in a single nucleotide sequence, the nucleotide sequence may comprise an open reading frame encoding AAV VP1 protein and an open reading frame encoding AAV VP3 protein.

In some embodiments, the insect cells may comprise a nucleotide sequence encoding adeno-associated virus (AAV) VP2 protein, but the VP2 initiation codon has been inactivated.

In some embodiments, the insect cells may further comprise a nucleotide sequence comprising at least one AAV inverted terminal repeat (ITR) nucleotide sequence and/or at least one nucleotide sequence encoding a gene product of interest. In some embodiments, the insect cells may further comprise a nucleotide sequence comprising a Rep78 or a Rep68 coding sequence operably linked to expression control sequences for expression in an insect cell. In some embodiments, the insect cells may further comprise a nucleotide sequence comprising a Rep52 or a Rep40 coding sequence operably linked to expression control sequences for expression in an insect cell.

In some embodiments, the AAV VP1 protein and the AAV VP3 protein are both encoded by a first nucleic acid construct. The first nucleic acid construct may additionally comprise a Rep78 or a Rep68 coding sequence operably linked to expression control sequences for expression in an insect cell. Additionally, or alternatively, the first nucleic acid construct may also additionally comprise a Rep52 or a Rep40 coding sequence operably linked to expression control sequences for expression in an insect cell. In some embodiments, the insect cell may further comprise a second nucleic acid construct comprising a second nucleotide sequence comprising, for example, at least one AAV inverted terminal repeat (ITR) nucleotide sequence and/or at least one nucleotide sequence encoding a gene product of interest. In some embodiments, the first and/or the second nucleic acid construct may be an insect cell-compatible vector, such as a baculoviral vector.

In another aspect, the present disclosure provides nucleic acid constructs comprising a nucleotide sequence encoding an AAV VP1 protein and AAV VP3 protein, wherein the nucleic acid construct does not express AAV VP2 protein, and wherein the nucleic acid sequence is operably linked to expression control sequences for expression in an insect cell.

In some embodiments, the nucleic acid construct may further comprise a Rep78 or a Rep68 coding sequence operably linked to expression control sequences for expression in an insect cell. In some embodiments, the nucleic acid construct may further comprise a Rep52 or a Rep40 coding sequence operably linked to expression control sequences for expression in an insect cell.

In some embodiments, the nucleotide sequence encoding the AAV VP1 protein and the AAV VP3 protein may be codon optimized for expression in an insect cell.

In another aspect, the present disclosure provides methods of increasing the capacity of an AAV gene therapy vector comprising expressing a nucleic acid construct that encodes an AAV VP1 and an AAV VP3, but not an AAV VP2, in an insect cell, thereby increasing the capacity of the AAV gene therapy vector relative to an AAV virion comprising VP1, VP2, and VP3 capsid proteins.

In another aspect, the present disclosure provides methods of increasing the genomic copy (gc) titer of an AAV gene therapy vector comprising expressing a nucleic acid construct that encodes an AAV VP1 and an AAV VP3, but not an AAV VP2, in an insect cell, thereby increasing the copy number titer of the AAV gene therapy vector relative to an AAV virion comprising VP1, VP2, and VP3 capsid proteins. Genomic copy titer in this sense referring to the amount of AAV capsid particles carrying a genomic copy of the rAAV vector genome, as determined by quantitative methods know in the art, e.g. by qPCR.

In another aspect, the present disclosure provides nucleic acid constructs comprising: a nucleotide sequence which comprises an open reading frame encoding an AAV VP1 protein; and a nucleotide sequence which comprises an open reading frame encoding an AAV VP3 protein; wherein the open reading frames encoding the AAV VP1 protein and the AAV VP3 protein are operably linked to expression control sequences for expression in an insect cell, and wherein AAV VP2 protein is not encoded by the nucleic acid construct.

In some embodiments, the open reading frame encoding AAV VP3 protein overlaps with the open reading frame encoding AAV VP1 protein. In some embodiments, the open reading frames encoding the AAV VP1 protein and the AAV VP3 protein are organized such that the AAV VP1 protein and the AAV VP3 protein are transcribed as a single RNA transcript upon expression. In some embodiments, the open reading frame encoding AAV VP3 protein and the open reading frame encoding AAV VP1 protein are transcribed from separate expression cassettes. In some embodiments, the open reading frame encoding AAV VP3 protein and the open reading frame encoding AAV VP1 protein are transcribed from a single expression cassette.

In another aspect, the present disclosure provides methods of increasing the capacity of an AAV gene therapy vector comprising expressing in an insect cell a nucleic acid construct comprising: a nucleotide sequence which comprises an open reading frame encoding an AAV VP1 protein; and a nucleotide sequence which comprises an open reading frame encoding an AAV VP3 protein; wherein the open reading frames encoding the AAV VP1 protein and the AAV VP3 protein are operably linked to expression control sequences for expression in an insect cell, and wherein AAV VP2 protein is not encoded by the nucleic acid construct, thereby increasing the capacity of the AAV gene therapy vector relative to an AAV virion comprising VP1, VP2, and VP3 capsid proteins.

In another aspect, the present disclosure provides methods of increasing the genomic copy titer of an AAV gene therapy vector comprising expressing in an insect cell a nucleic acid construct comprising: a nucleotide sequence which comprises an open reading frame encoding an AAV VP1 protein; and a nucleotide sequence which comprises an open reading frame encoding an AAV VP3 protein; wherein the open reading frames encoding the AAV VP1 protein and the AAV VP3 protein are operably linked to expression control sequences for expression in an insect cell, and wherein AAV VP2 protein is not encoded by the nucleic acid construct, thereby increasing the genomic copy titer of the AAV gene therapy vector relative to an AAV virion comprising VP1, VP2, and VP3 capsid proteins.

In another aspect, the present disclosure provides AAV virions produced in an insect cell, said insect cell comprising: a first nucleic acid sequence encoding at least one gene product of interest and at least one ITR; a second nucleic acid encoding an AAV VP1 protein, the second nucleic acid being operably linked to an expression control sequence for expressing of AAV VP1 in an insect cell; and a third nucleic acid encoding an AAV VP3 protein, the third nucleic acid being operably linked to an expression control sequence for expressing of AAV VP3 in an insect cell; a fourth nucleic encoding AAV Rep proteins; wherein the AAV virion comprises a capsid comprising an AAV VP1 protein and an AAV VP3 protein but does not comprise an AAV VP2 protein.

In some embodiments, the first nucleotide sequence is positioned between two AAV ITR nucleotide sequences.

In some embodiments, the gene of interest is a therapeutic gene. For example, the therapeutic gene may be a gene encoding Factor VIII or a microRNA, siRNA, or shRNA targeting a disease-causing gene.

In some embodiments, the AAV virion is selected from the group consisting of AAV serotype 1 (AAV1), AAV2, AAV3, AAV4, AAV5, AAV6, AAV7, AAV8, AAV9, AAV10, and AAV11, AAV12, AAV13. In some embodiments, the AAV virion is a recombinant AAV (rAAV), such as an rAAV2/5 that comprises at least a portion of AAV2 and AAV5. In some embodiments, the AAV virion is a chimeric AAV (AAV$^{ch}$), such as a chimeric AAV serotype 5 (AAV5$^{ch}$). In some embodiments, the AAV virion is a mutant or variant AAV.

In some embodiments, the ratio of VP1 protein to VP3 protein is between about 1:5 and about 1:59. In one embodiment, the ratio of VP1 to VP3 is more than 1:59.0, or, more specifically, the ratio of VP1 protein to VP3 protein may be about 1:10. The ratio of VP1 protein to VP3 protein may preferably be about 1:5. The ratio of VP1 to VP3 can be easily determined by detecting VP1 and VP3 protein on gel, e.g. with an antibody, or with general protein staining, and measuring the intensity of the staining which is representative of amount of protein. Also, Direct Liquid Chromatography/Mass Spectrometry Analysis or the like may be contemplated to detetermine the ratio of VP1 to VP3, (Jin et al. Hum Gene Ther Methods. 2017 October; 28 (5):255-267).

In some embodiments, the disclosed AAV virions may be incorporated into a pharmaceutical composition.

In another aspect, the present disclosure provides methods for producing recombinant AAV virion in an insect cell comprising: culturing insect cells that express AAV VP1 protein and AAV VP3 protein, but do not express AAV VP2 protein under conditions that permit production of the recombinant AAV virion; and recovering the recombinant AAV virion from the culture.

In some embodiments, the capacity of the AAV virion is increased relative to an AAV virion comprising VP1, VP2, and VP3 capsid proteins.

In some embodiments, the culture has an increased genomic copy titer of the recombinant AAV virion relative to the genomic copy titer achieved by culturing an AAV virion comprising VP1, VP2, and VP3 capsid proteins under the same conditions.

In some embodiments, the culture will yield an AAV virion with a ratio of VP1 protein to VP3 protein is between about 1:5 and about 1:20, or, more specifically, with a ratio of VP1 protein to VP3 protein is about 1:5.

In another aspect, the present disclosure provides methods of increasing expression of a gene of interest in a subject, comprising, administering to the subject a therapeutically effective amount of a disclosed VP2-less virion, thereby increasing expression of the gene of interest encoded in the AAV virion genome.

In some embodiments, the gene of interest is a therapeutic gene.

In some embodiments, the subject is a human subject.

In another aspect, the present disclosure provides methods of treating a genetic disease in a subject comprising, administering to a subject with a genetic disease a therapeutically effective amount of a recombinant AAV virion, the recombinant AAV virion comprising in its genome a first nucleic acid sequence encoding at least one therapeutic gene; wherein the AAV virion comprises a capsid comprising an AAV VP1 protein and an AAV VP3 protein but does not comprise an AAV VP2 protein and wherein the AAV virion has been produced in insect cells.

In some embodiments, the therapeutic gene encodes a protein that is mutated or deficient in the genetic disease. In some embodiments, the therapeutic gene is a microRNA, siRNA, or shRNA targeting a genetic disease-causing gene.

In some embodiments, the genetic disease may be a Factor VIII deficiency, and therefore, the therapeutic gene may be a Factor VIII gene. In some embodiments, the genetic disease may be a form of hemophilia (e.g., hemophilia A or hemophilia B) or a clotting disorder, and therefore the therapeutic gene may be a gene encoding a clotting factor that is deficient or mutated in the clotting disorder. In some embodiments, the genetic disease may be Huntington's disease, and therefore the therapeutic gene may be a microRNA, siRNA, or shRNA that targets a mutated Huntingtin gene.

In some embodiments, the genetic disease may be selected from acute intermittent porphyria (AIP), age-related macular degeneration, Alzheimer's disease, arthritis, Batten disease, Canavan disease, Citrullinemia type 1, Crigler Najjar, congestive heart failure, cystic fibrosis, Duchene muscular dystrophy, dyslipidemia, glycogen storage disease type I (GSD-I), hemophilia A, hemophilia B, hereditary emphysema, homozygous familial hypercholesterolemia (HoFH), Huntington's disease (HD), Leber's congenital amaurosis, methylmalonic academia, ornithine transcarbamylase deficiency (OTC), Parkinson's disease, phenylketonuria (PKU), spinal muscular atrophy, paralysis, Wilson disease, epilepsy, Pompe disease, amyotrophic lateral sclerosis (ALS), Tay-Sachs disease, hyperoxaluria 9PH-1), spinocerebellar ataxia type 1 (SCA-1), SCA-3, u-dystrophin, Gaucher's types II or III, arrhythmogenic right ventricular cardiomyopathy (ARVC), Fabry disease, familial Mediterranean fever (FMF), proprionic acidemia, fragile X syndrome, Rett syndrome, Niemann-Pick, and Krabbe disease.

The following detailed description is exemplary and explanatory, and is intended to provide further explanation of the invention.

BRIEF DESCRIPTION OF THE DRAWINGS

FIG. 3A shows AAV comprising a SEAP transgene and FIG. 3B shows AAV comprising a FVIII transgene.

DETAILED DESCRIPTION

Figure 1:
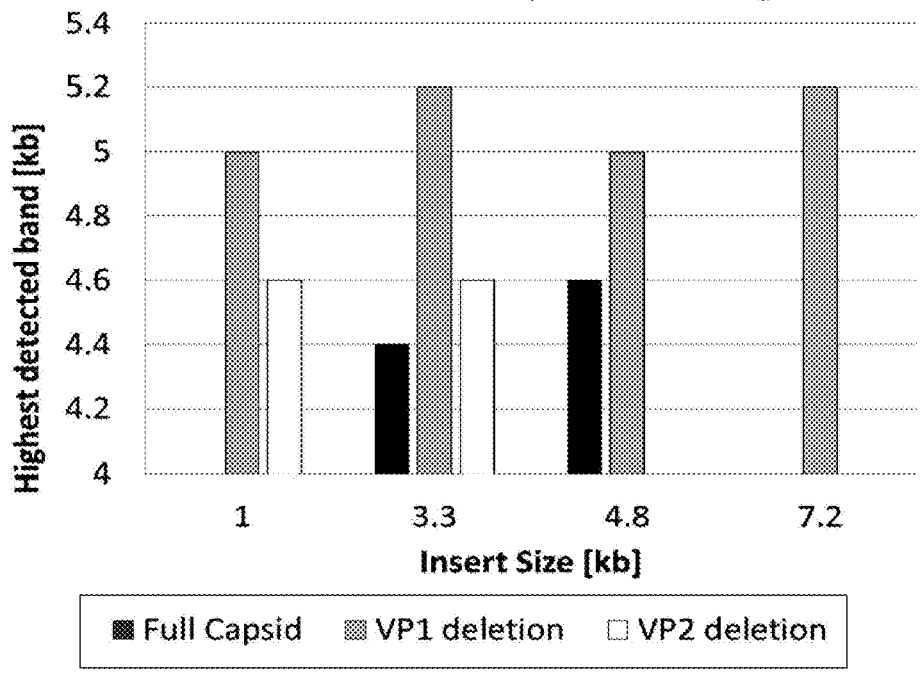
FIG. 1 shows that the packaging capacity of AAV increases significantly with deleted VP1, but that there is no significant increase in packaging with deleted VP2 as compared to wild-type AAV5 (AAV 765), which possesses a full capsid. The graph shows the highest detected band on a formaldehyde gel for AAV5, ΔVP1, and ΔVP2 for differently sized transgenes. The transgenes used are microRNA (1 kb, 3.3 kb, 4.8 kb) and Factor VIII (7.2 kB).

Described herein are VP2-less rAAV produced in insect cells, insect cells for producing VP2-less rAAV, and methods of making and using the same. The disclosed compositions and methods are improvements over the state of the art, as they provide a means of increasing production efficiency and packaging capacity of rAAV that will allow for feasible commercial scale up of virus particles that maintain therapeutic potency.

I. Definitions

In this document and in its claims, and in its clauses, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one."

As used herein, the term "capsid" refers to the protein coat of the virus or viral vector. The term "AAV capsid" refers to the protein coat of an adeno-associated virus (AAV), which is composed of a total of about 60 subunits of viral protein 1 (VP1), VP2, and/or VP3.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the terms "recombinant parvoviral vector," "recombinant andeno-associated Virus vector," and "rAAV vector" refer to vectors comprising one or more polynucleotide sequences of interest flanked by parvoviral or AAV nucleic acid sequences (e.g., Rep sequences, ITPs, VP genes, etc.). Such vectors can be replicated and packaged into infectious viral particles when present in an insect host cell that is expressing AAV rep and cap gene products. When an rAAV vector is incorporated into a larger nucleic acid construct (e.g., a plasmid or baculovirus used for cloning or transfection), then the rAAV vector is typically referred to as a "pro-vector" which can be "rescued" by replication and encapsulation in the presence of AAV packaging functions and necessary helper functions.

As used herein, the term "operably linked" refers to a linkage of polynucleotide or polypeptide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Nucleic acid sequences that are operably linked are typically contiguous, and, where necessary to join two protein encoding regions, may be in the same reading frame. However, those of skill in the art will appreciate that nucleic acid sequences may affect transcription of distal sequences as well.

As used herein, the term "expression control sequence" refers to a nucleic acid sequence that regulates the expression of another nucleotide sequence to which the expression control sequence is operably linked. An expression control sequence is "operably linked" to a nucleotide sequence when the expression control sequence controls and/or regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons.

The term "expression control sequence" may include, but is not limited to, a sequence whose presence are designed to influence expression, and can also include additional advantageous components. For example, leader sequences and fusion partner sequences are expression control sequences. The term can also include the design of the nucleic acid sequence such that undesirable, potential initiation codons in and out of frame are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which affect the translation, e.g., Kozak sequences, are known in insect cells. Expression control sequences can be of such nature as to modulate the nucleotide sequence to which it is operably linked such that lower expression levels or higher expression levels are achieved.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A constitutive promoter is a promoter that is active in most tissues under most physiological and developmental conditions. An inducible promoter is a promoter that is physiologically or developmentally regulated, for example, by the application of a chemical inducer or a specific condition (e.g., a hypoxia-induced promoter). A tissue specific promoter is only active in specific types of tissues or cells. Each of these specific promoter types have been contemplated for the purposes of the present disclosure and may be incorporated into the disclosed rAAV in order to control transcription of one or more genes of interest within the rAAV.

As used herein, the terms "ITR" or "inverted terminal repeat" refer to nucleic acid sequences that exist in AAV and/or rAAV that can form a T-shaped palindromic structure, which is generally required for completing AAV lytic and latent life cycles.

As used herein, the term "gene cassette" refers to a fragment of DNA carrying, and capable of expressing, one or more genes or coding sequences of interest between one or more sets of restriction sites. A gene cassette can be transferred from one DNA sequence (often in a plasmid vector) into another by "cutting" the fragment out using restriction enzymes and ligating it back into a new vector, for example, into a new plasmid backbone.

As used herein, the term "therapeutic gene" refers to any gene or nucleic acid that can be used for treating a disease in a subject. A therapeutic gene may encode a protein that is deficient, mutated, dysfunctional, or otherwise aberrant in a subject, or a therapeutic gene may encode a functional nucleic acid, such as a short interfering RNA (siRNA, micro RNA (miRNA), or short hairpin RNA (shRNA), which may be used to prevent transcription and/or translation of a gene that is mutated or pathologically up-regulated in a disease.

As used herein, the term "subject" includes humans and non-human animals. Non-human animals include all vertebrates (e.g., mammals and non-mammals) such as, non-human primates (e.g., cynomolgus monkey), mice, rats, sheep, dogs, cows, chickens, amphibians, and reptiles. Except when specifically noted, the terms "patient" or "subject" are used herein interchangeably.

As used herein, the term "treating" or "treatment" of any disease or disorder refers, to ameliorating the disease or disorder such as by slowing or arresting or reducing the development of the disease or at least one of the clinical symptoms thereof. "Treating" or "treatment" can also refer to alleviating or ameliorating or improving at least one physical or physiological parameter associated with a disease, including those which may not be discernible by the patient. Thus, "treating" or "treatment" can refer to modulating the disease or disorder, either physically (e.g., stabilization of a discernible symptom), physiologically (e.g., stabilization of a physical parameter), or both.

As used herein, the phrases "therapeutically effective amount" means an amount of recombinant AAV virion administered to a subject that provides the specific pharmacological effect for which the AAV virions are being administered. It is emphasized that a therapeutically effective amount of AAV virions will not always be effective in treating a disease or disorder in a given subject, even though such concentration is deemed to be a therapeutically effective amount by those of skill in the art. For convenience only, exemplary amounts are provided below.

II. Parvoviridae and AAV

Viruses of the Parvoviridae family are small DNA viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus *Dependovirus*. As may be deduced from the name of their genus, members of the Dependovirus are unique in that they usually require co-infection with a helper virus such as adenovirus or herpes virus for productive infection in cell culture. The genus *Dependovirus* includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, etc.).

The genomic organization of all known AAV serotypes is very similar, and therefore the disclosed method of making a VP2-less AAV may be applied to any AAV serotype. The genome of AAV is a linear, single-stranded DNA molecule that is less than about 5,000 nucleotides in length. Inverted terminal repeats (ITRs) flank the coding nucleotide sequences for the non-structural replication (Rep) proteins and the structural (VP) proteins. The VP proteins (VP1, -2, and -3) form the capsid. The terminal 145 nucleotides are self-complementary and are organized so that an energetically stable intramolecular duplex forming a T-shaped hairpin may be formed. These hairpin structures function as an origin for viral DNA replication, serving as primers for the cellular DNA polymerase complex. Following wild type AAV infection in mammalian cells the Rep genes (e.g., Rep78 and Rep52) are expressed from a P5 promoter and a P19 promoter, respectively, and both Rep proteins have a function in the replication of the viral genome. A splicing event in the Rep ORF results in the expression of four Rep proteins—Rep78, Rep68, Rep52 and Rep40. However, it has been shown that the unspliced mRNA encoding Rep78 and Rep52 proteins is sufficient for AAV vector production in mammalian and insect cells.

III. Method of Making VP2-Less AAV in Insect Cells

Warrington et al., J Virol. 78: 6595-6609 (2004) found that AAV virions with deleted VP2 could be formed in mammalian production systems. In insect cells, however, VP2 was conventionally believed to be essential for AAV capsid formation. See Ruffing et al., J. Virol. 66: 6922-6930 (1992). In Ruffing et al. (1992, supra) it was found that whenever VP2 was deleted, no empty virus-like particles were formed in insect cells. These studies suggested that making VP2-less AAV particles would not be a viable strategy for producing AAV in insect cells. Surprisingly, however, the present disclosure reveals that an AAV particle comprising VP1 and VP3 without VP2 can be produced in insect cells, and that the VP2-less AAV particles has both an increased capacity for packaging larger gene inserts and improved production efficiency for large scale manufacturing. Further, the present disclosure indicates that batches of VP2-less AAV that are produced in insect cells possess more homogeneous capsids (i.e., the ratio and composition of VP1 and VP3 proteins of the viral capsids is more consistent) than AAV comprising VP1, VP2, and VP3.

The various modifications of the AAV viral vectors described herein can be achieved by application of well-known genetic engineering techniques such as those described in Sambrook and Russell, "Molecular Cloning: A Laboratory Manual" (3rd edition, Cold Spring Harbor Laboratory Press, Cold Spring Harbor, N.Y., 2001). Various further modifications of coding regions are known to the skilled artisan.

Techniques known to one skilled in the art for expressing foreign genes in insect host cells can be used to practice the methods of the present disclosure. Exemplary methodologies for molecular engineering and expression of polypeptides in insect cells is described, for example, in Summers and Smith, "A Manual of Methods for Baculovirus Vectors and Insect Culture Procedures," (Texas Agricultural Experimental Station Bull. No. 7555, 1986); Luckow "Cloning and Expression of Heterologous Genes in Insect Cells with Baculovirus Vectors' Recombinant DNA Technology and Applications," (McGraw-Hill, N.Y., 1991); in King and Possee, "The Baculovirus Expression System," (Chapman and Hall, 1992); O'Reilly et al., "Baculovirus Expression Vectors: A Laboratory Manual," (Oxford University Press, 1993); U.S. Pat. No. 4,745,051; US2003/148506; and WO03/074714. Suitable promoters for transcription may include, but are not limited to, an LP1 liver-specific promoter, P5, P19, P40, polyhedron (PolH), 4×Hsp27 EcRE+ minimal Hsp70 promoter, p10, p35, IE-1, ΔIE-1 promoters, and further promoters described in the above references.

For the purposes of the present disclosure, an insect cell can comprise a single nucleotide sequence encoding AAV VP1 and AAV VP3 or distinct, non-contiguous nucleotide sequence encoding AAV VP1 and AAV VP3. In wild-type AAV the three capsid proteins are produced in an overlapping fashion from the cap open reading frame by using alternative mRNA splicing of the transcript and alternative translational start codons. A common stop codon is employed for all three proteins. Accordingly, site directed mutagenesis of the individual start codons can be used to make AAV missing expression of one or more of the individual VP1, VP2, or VP3. Thus, for the purpose of the present disclosure, an insect cell may comprise a nucleotide sequence encoding AAV VP2 protein, so long as the VP2 initiation codon is inactivated or not functional and VP2 is not produced. Inactivation may include changing the start codon to an alternative codon that does not function as a start codon in insect cells. Inactivation may include changing the start codon to a codon for alanine, or the like, that does not function as a start codon, The insect cell may comprise two separate nucleic acid constructs, one for each of the first and second nucleotide sequences, or the insect cell may comprise a single type of nucleic acid construct comprising both the first and second nucleotide sequences. Accordingly, the inventors of the present disclosure found that the VP2-less AAV can be made by combining a first nucleotide sequence encoding AAV VP1 protein and a separate, second nucleotide sequence encoding AAV VP3 protein. In some embodiments, the insect cell of the invention comprises a single nucleotide sequence comprising an open reading frame encoding AAV VP1 protein and an open reading frame encoding AAV VP3 protein.

For the purpose of the present disclosure, the precise organization of a VP1 coding sequence and a VP3 coding sequence within a given construct or constructs is not particularly limited. In some embodiments, a nucleic acid construct encoded a disclosed VP2-less AAV may comprise (a) a nucleotide sequence comprising an open reading frame encoding an AAV VP1; and, (b) a nucleotide sequence comprising an open reading frame encoding AAV VP3; wherein the open reading frames encoding the AAV VP1 and the AAV VP3 are operably linked to expression control sequences for expression in an insect cell. Alternatively, the open reading frame encoding AAV VP3 can overlap with the open reading frame encoding AAV VP1 in this nucleic acid construct, or the open reading frames encoding the AAV VP1 and the AAV VP3 can be organized such that the AAV VP1 and the AAV VP3 are transcribed as a single RNA transcript upon expression. In some embodiments, the open reading frame encoding AAV VP3 and the open reading frame encoding AAV VP1 can be transcribed from separate expression cassettes or from a single expression cassette.

Infectivity of AAV particles may depend, at least in part, on the presence of inverted terminal repeat (ITRs) sequences present in the AAV, as ITRs are important for completing AAV lytic and latent life cycles. Hence, the inventors of the present disclosure provide an insect cell comprising a nucleotide sequence comprising at least one AAV inverted terminal repeat (ITR) nucleotide sequence and at least one nucleotide sequence encoding a gene product of interest.

For the purposes of the present disclosure, the vectors used to produce rAAV in insect cells are generally insect cell-compatible vectors. An "insect cell-compatible vector" is a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome or it may be transient. The vectors can be introduced by any means known, for example by chemical treatment of the cells, electroporation, or infection. In some embodiments, the vector used to produce AAV in an insect cell is a baculovirus, a viral vector, or a plasmid. Baculoviral vectors and methods for their use are generally known in the art. See, e.g., Smith et al., Mol. Ther., 17 (11): 1888-96 (2009). In some embodiments, the nucleotide sequences encoding VP1 and VP3 are codon optimized for expression in an insect cell using methods such as those disclosed in U.S. 2016-0032254 A1.

Similarly, the choice of serotype of the AAV, while important for successful gene delivery to specific target organs and cells in a subject, is not particularly limited for the purposes of the disclosed methods of making a VP2-less AAV in an insect cell. The serotype of the AAV can determine internalization of the AAV and subsequent transgene expression in specific organs and cells because the surface of the AAV capsid functions in the process of target cell binding, subsequent internalization, and intracellular trafficking. AAV is able to infect a number of mammalian cells, and the cellular tropicity of AAV differs among serotypes. For example, there are differences in mammalian CNS cell tropism and transduction efficiency among, for example, AAV2, AAV4, and AAV5, and therefore the selection of the particular serotype maybe depend of the disease that is intended for treatment or the target cell type. The AAV serotype may also influence packaging capacity and production efficiency (FIGS. 7 and 8), with certain serotypes being more efficient in packing smaller or larger genes of interest.

AAV sequences that may be used for producing VP2-less AAV in insect cells can be derived from the genome of any AAV serotype. Generally, the AAV serotypes have genomic sequences of significant homology at the amino acid and the nucleic acid levels, which perform an identical set of genetic functions and produce virions that are physically and functionally very similar. AAV of different serotypes also replicate and assemble by practically identical mechanisms. The genetic sequence information of the disclosed AAV serotypes is generally known in the art. See, e.g., GenBank Accession number U89790; GenBank Accession number J01901; GenBank Accession number AF043303; GenBank Accession number AF085716; Chlorini et al., J. Virol. 71: 6823-33 (1997); Srivastava et al., J. Vir. 45:555-64 (1983); Chlorini et al., J. Vir. 73:1309-1319 (1999); Rutledge et al., J. Vir. 72:309-319 (1998); and Wu et al., J. Vir. 74: 8635-47 (2000).

Thus, for the purposes of the present disclose, a VP2-less AAV may be selected from the group consisting of AAV serotype 1 (AAV1), AAV2, AAV3, AAV4, AAV5, AAV6, AAV7, AAV8, AAV9, AAV10, AAV11, AAV12 and AAV13. In some embodiments, it may be preferable for the VP2-less AAV to be derived from AAV1 or AAV5. In some embodiments, it may be preferable for the VP2-less AAV to be derived from AAV6, AAV7, AAV8, AAV9, or AAV10.

In addition to the aforementioned naturally evolved AAV serotypes, several strategies to engineer hybrid AAV serotype vectors have been formulated in recent years. For example, rAAV2/5 comprise at least a portion of AAV2 and AAV5. In particular, an rAAV5 may contain the genome of serotype 2 packaged in the capsid from serotype 5. Similar AAV hybrids include, but are not limited to AAV2/8 and AAV2/9. In some embodiments, the disclosed VP2-less AAV may also be a chimeric AAV (AAV$^{ch}$), such as a chimeric AAV serotype 5 (AAV5$^{ch}$). For example, an AAV may comprise a VP1 capsid protein from one serotype and a VP3 capsid protein from another serotype. (see i.a. Choi et al. Curr Gene Ther. 2005 June; 5 (3): 299-310). The AAV virion described above can also be a mutant or variant AAV. In some embodiments, the disclosed VP2-less AAV may be mutant or variant AAV, in which at least one nucleic acid or amino acid has been substituted, inserted, or deleted relative to a corresponding wild-type sequence. In one embodiment the VP1 protein is a hybrid VP1 protein, with the N terminus derived from one serotype, whereas the VP3 protein sequence, as also comprised in the hybrid VP1 protein is from another serotype. For example, the N-terminal portion of type 5 VP1 can be replaced with the equivalent portion of type 2 to generate infectious AAV5 particles (Urabe et al. J Virol. 2006 February; 80 (4): 1874-1885).

In some embodiments, a VP2-less AAV virion can be produced in an insect cell comprising: a first nucleic acid sequence encoding at least one gene product of interest; a second nucleic acid encoding an AAV VP1 operably linked to an expression control sequence for expressing the AAV VP1 in an insect cell; a third nucleic acid encoding an AAV VP3 protein operably linked to an expression control sequence for expressing the AAV VP3 in an insect cell; and a fourth nucleic acid encoding an AAV Rep protein operably linked to an expression control sequence for expression in an insect cell. Thus, the AAV virions produced by the disclosed insect cell will have a capsid comprising VP1 and VP3, but not VP2. In further embodiments, the first nucleotide sequence may be positioned between two AAV ITR sequences.

The present disclosure further provides methods for producing recombinant AAV virions in an insect cell comprising culturing the insect cell expressing AAV VP1 and AAV VP3, but not AAV VP2 under conditions that permit production of the recombinant AAV virion; and recovering the recombinant AAV virion from the culture. The disclosed methods allow for the production of a recombinant AAV virion, wherein the packaging capacity and the genomic copy titer of the VP2-less AAV virion is increased relative to an AAV virion comprising VP1, VP2, and VP3 capsid proteins. In some embodiments, the ratio of VP1 to VP3 in the disclosed VP2-less AAV capsid is between about 1:5 and about 1:10. More specifically, the ratio of VP1 to VP3 may be about 1:5, about 1:6, about 1:7, about 1:8, about 1:9, or about 1:10.

IV. Deleting VP2 Improves Capacity and Production Efficiency of AAV

Figure 3B:
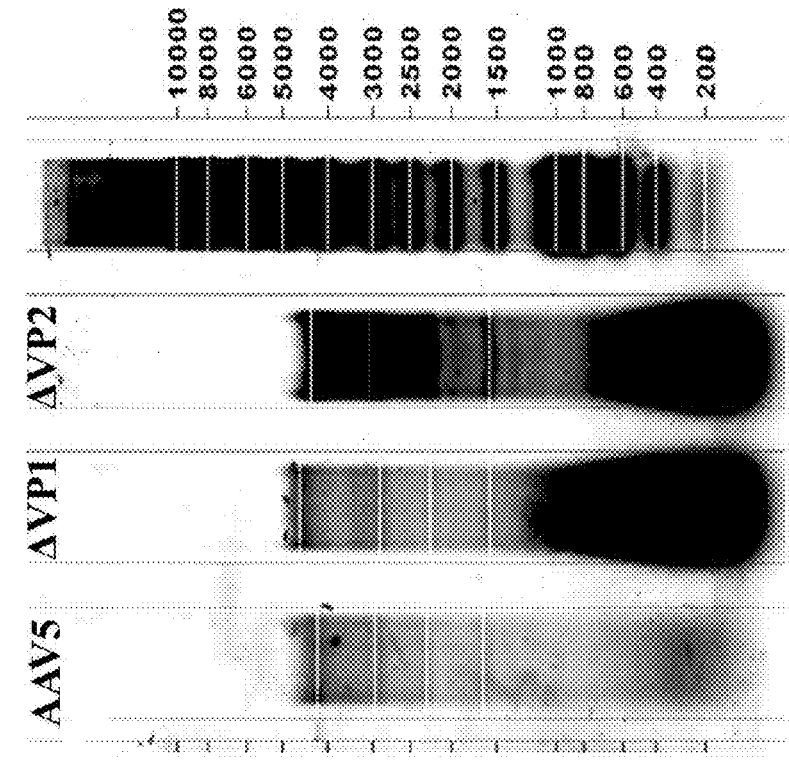
FIGS. 3A-3B show the formaldehyde gels of AAV5, ΔVP1, ΔVP2.
Figure 3A:
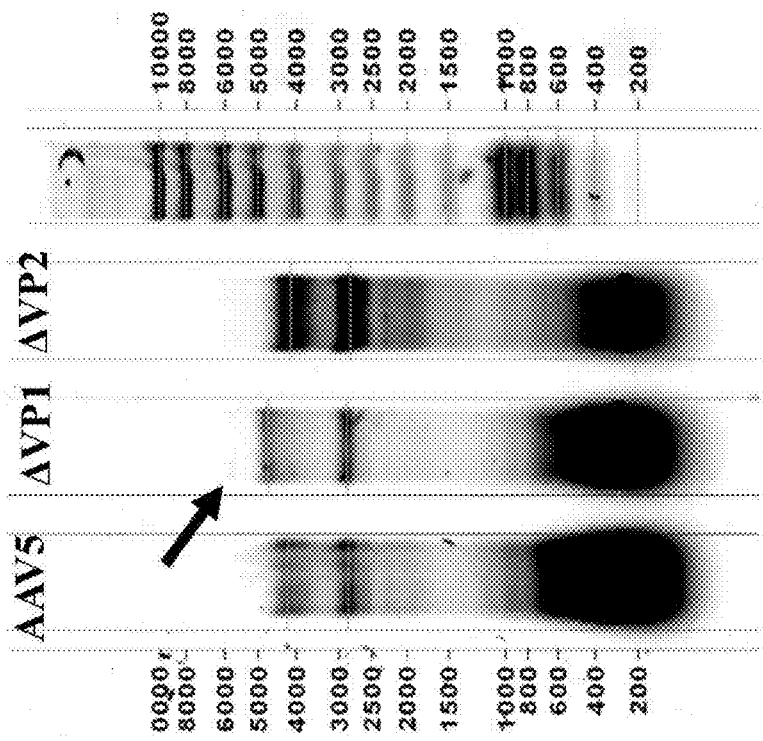
Figure 4:
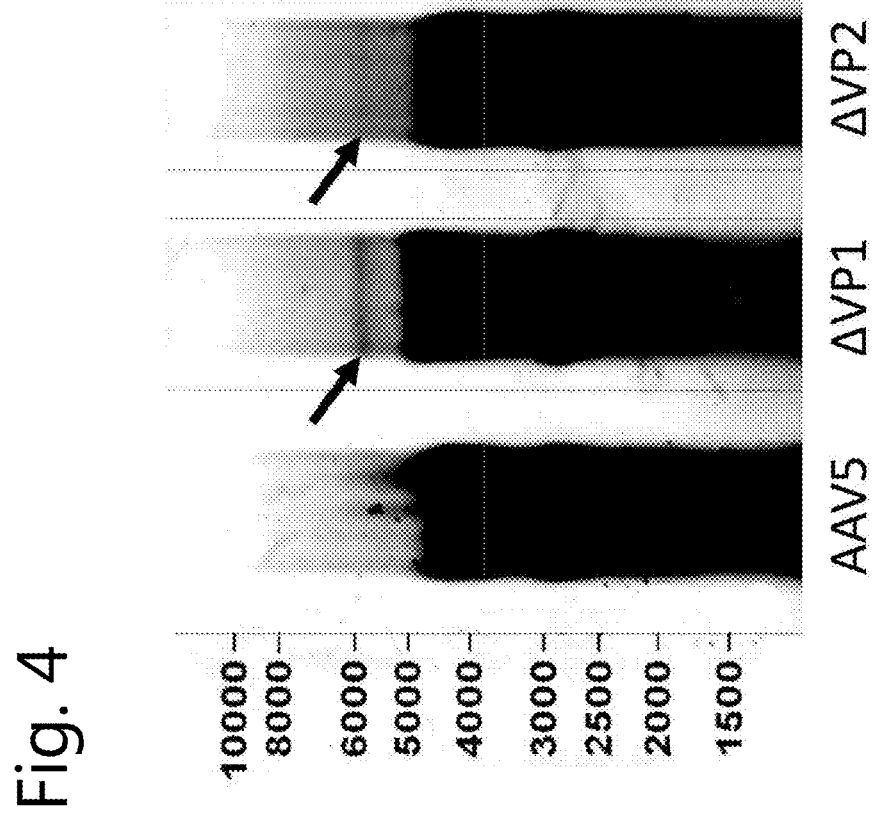
FIG. 4 is an over exposure of FIG. 3A which shows that ΔVP1 and ΔVP2 can package the same amount and significantly more than 765.
Figure 6:
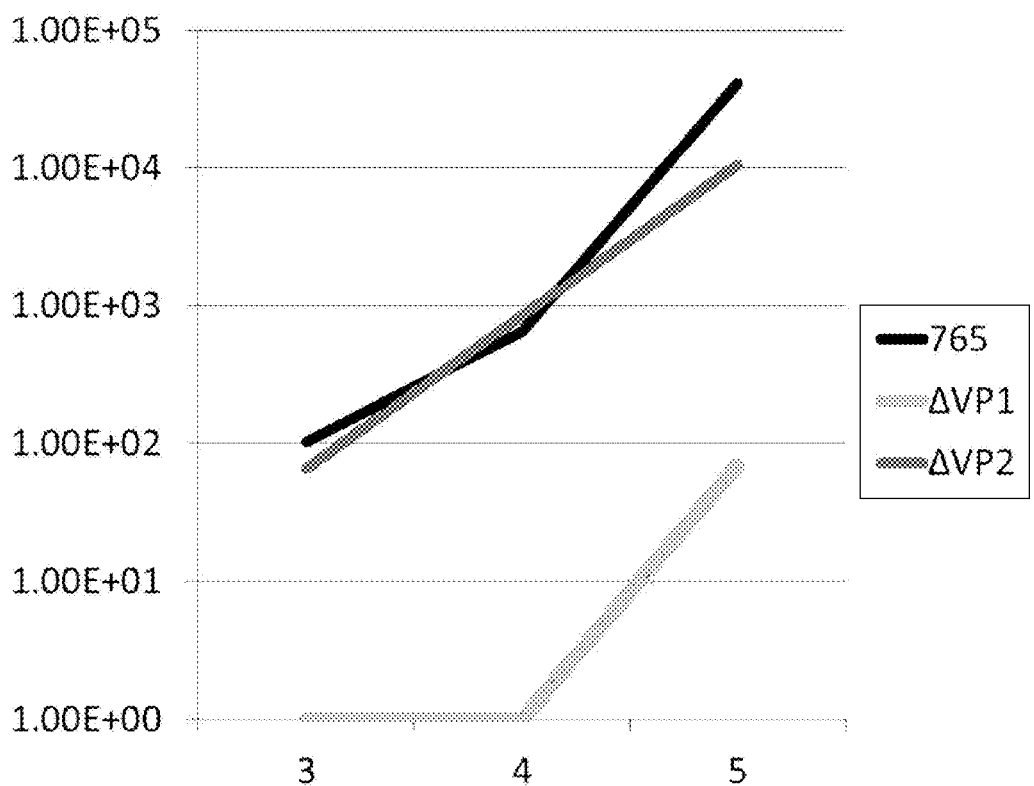
FIG. 6 shows that deletion of VP1 leads to complete loss of potency; whereas viruses are still potent and capable of transfection with VP2 is deleted. Potency was measured by performing a SEAP Assay in Huh7 cells. The graphs show potency of AAV5 with and without VP1, VP2.

The disclosed VP2-less AAV produced in insect cellscan package significantly more genomic material with its capsid than a wild-type AAV5 possessing a capsid composed of VP1, VP2, and VP3. Deleting VP2 did not increase the capacity of the AAV to package larger gene inserts; rather, VP2 deletion allowed packaging of larger amount of vectors or overall genetic material (FIGS. 3 and 4). It was determined that deleting VP1 can also increase the capacity to package larger genes and more genetic material; however, VP1-less AAVs are non-infectious (FIG. 6), thus limiting their potential utility as gene therapy vectors. In contrast, deleting VP2 did not affect infectivity of the resulting AAV virions. Thus, the disclosed VP2-less AAV as produced in insect cells possess multiple physical properties (i.e., increased payload capacity and maintained infectivity/potency) that make the disclosed VP2-less AAV particularly well suited for gene therapy.

Accordingly, the present disclosure provides methods of increasing the capacity of an AAV gene therapy vector comprising a nucleic acid construct comprising a nucleotide sequence encoding an AAV VP1 and AAV VP3, wherein the nucleic acid construct does not express AAV VP2 protein, and wherein the nucleic acid sequence is operably linked to expression control sequences for expression in an insect cell. An AAV with a capsid comprising only VP1 and VP3 has an increased capacity (FIG. 4) compared to an AAV virion with a capsid comprising VP1, VP2, and VP3.

Moreover, the disclosed VP2-less AAV can also be produced more efficiently than wild-type AAV or VP1-less AAV. Indeed, insect cells carrying one of the VP2-less AAV viral vectors produced higher titers of isolated AAV virions than AAV5 possessing a capsid composed of VP1, VP2, and VP3. This effect was predominantly seen when packing larger transgenes like a gene encoding FVIII (7.2 kb), but the results are nevertheless unexpected as previous research in mammalian expression systems failed to result in virions with increased capacity (Grieger (2005, supra)) and previous attempts to produce VP2-less AAV virions in an insect cell system failed altogether (Ruffing et al. (1992, supra).

Because the disclosed VP2-less AAV have an increased packaging capacity, the size of the gene(s) of interest that are packaged within the virions are not as limited as conventional AAV. For example, the disclosed VP2-less AAV may comprise a gene or genes of interest that are about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, or about 10 or more kilobases (kb).

Additionally, the production efficiency of the disclosed VP2-less AAV is significantly increased relative to wild-type AAV. Thus, in some embodiments, the genomic copy titer of the disclosed VP2-less AAV produced in insect cells may be about 1, about 1.25, about 1.5, about 1.75, about 2, about 2.25, about 2.5, about 2.75, about 3, about 3.25, or about 3.5 or more logs higher than the genomic copy titer of a wild-type AAV with VP2 of a corresponding serotype under the same or similar culturing conditions.

A further benefit of the disclosed methods of producing VP2-less AAV in an insect cell is that the virions are more homogeneous. Under normal circumstances in a wild-type AAV with a capsid comprising all three capsid proteins, the distribution of the proteins within the capsid is usually roughly 1:1:10 (VP1:VP2:VP3), respectively), but the precise makeup occurs by chance along a Poisson distribution. This means that the ratio of 1:1:10 may be regarded as an average capsid compostion. Removing VP2 decreases the potential combinatorial outcomes and thus results in a population of AAV virions that are more uniform and homogeneous. This is beneficial from both a clinical and a regulatory perspective, as it is always desirable to be able to produce consistent, uniform batches of therapeutic products and to limit batch-to-batch variability. The disclosed methods accomplish this by producing VP2-less AAV in which the ratio of VP1 to VP3 in the capsid is between about 1:4 and about 1:59. For example, the ratio of VP1 to VP3 can be about 1:4, about 1:5, about 1:6, about 1:7, about 1:8, about 1:9, about 1:10, and about 1:11. Hence, as an AAV capsid consists of about 60 VP proteins, of which the average number of VP1 proteins per AAV capsid may range from 1 to 15 per capsid.

V. Methods of Treating Disease with VP2-Less AAV

The present disclosure also provides methods of treating human diseases using the disclosed VP2-less AAV virions. Thus, in some embodiments the VP2-less AAV virion is a pharmaceutical composition. The disclosed methods of treatment are generally applicable to human subjects, but may be extended to non-human animals as well.

The diseases that can be treated using the disclosed VP2-less AAV will generally be diseases caused by a defective or mutated gene or by defective or aberrant gene expression. Defective gene expression can include reduced expression (i.e., down-regulation) or increased expression (i.e., up-regulation) of a given gene relative to normal gene expression levels for that gene. Furthermore, defective gene expression can involve a failure of an inducible or tissue specific gene to respond to internal or external physiological signals that should activate or inactive gene expression.

When a disease is caused by down-regulation of a target gene or a deficiency of the gene product, the present disclosure provides a method of increasing expression of the target gene in a subject, comprising, administering to the subject a therapeutically effective amount of the VP2-less AAV virion produced in an insect cell and comprising the gene of interest, thus resulting in increased expression of the target gene in the subject. By the same token, when a disease is caused by up-regulation of a target gene or an excess of the gene product, the present disclosure provides a method of decreasing expression of the target gene in a subject, comprising, administering to the subject a therapeutically effective amount of the VP2-less AAV virion comprising a gene of interest, wherein the gene of interest is a therapeutic RNA that interferes with transcription and/or translation of the target gene, resulting in decreased expression of the target gene in the subject.

Generally, the gene of interest encoded by the disclosed VP2-less AAV is a therapeutic gene. A therapeutic gene may correspond to a gene that is pathologically down-regulated in a subject or encode a protein that is deficient or mutated in the subject. Alternatively, a therapeutic gene can encode a microRNA, siRNA, or shRNA to interfere with transcription and/or translation of a gene that is over-expressed, a protein that is pathologically over-active, or a protein that is expressed in excess in a subject.

Thus, for the purposes of the present disclosure, the gene product of interest that may be expressed by the disclosed VP2-less AAV in a mammalian cell may encode a therapeutic gene product. A therapeutic gene product can be a polypeptide, or an RNAi agent, or other gene products that, when expressed in a target cell, provides a desired therapeutic effect such as, for example, ablation of an undesired activity or the complementation of a genetic defect. An RNAi agent or a "therapeutic RNA" is an RNA molecule that is capable of RNA interference such as a shRNA (short hairpin RNA) or an siRNA (short interfering RNA) or a miRNA (microRNA). siRNA, for example, generally comprise a short-length double-stranded RNA that are not toxic in mammalian cells Examples of therapeutic polypeptide gene products include, but are not limited to, cystic fibrosis transmembrane conductance regulator (CFTR), Factor IX, Factor VIII, Lipoprotein lipase (LPL or LPL S447X; see WO01/00220), Apolipoprotein A1, Uridine Diphosphate Glucuronosyltransferase (UGT), Retinitis Pigmentosa GTPase Regulator Interacting Protein (RP-GRIP), and cytokines or interleukins (e.g., IL-10), porphobilinogen deaminase (PBGD), and alanine: glyoxylate aminotransferase.

The diseases that can be treated according to the disclosed methods are not particularly limited, other than generally having a genetic cause or basis. For example, the disease that may be treated with the disclosed methods may include, but are not limited to, acute intermittent porphyria (AIP), age-related macular degeneration, Alzheimer's disease, arthritis, Batten disease, Canavan disease, Citrullinemia type 1, Crigler Najjar, congestive heart failure, cystic fibrosis, Duchene muscular dystrophy, dyslipidemia, glycogen storage disease type I (GSD-I), hemophilia A, hemophilia B, hereditary emphysema, homozygous familial hypercholesterolemia (HoFH), Huntington's disease (HD), Leber's congenital amaurosis, methylmalonic academia, ornithine transcarbamylase deficiency (OTC), Parkinson's disease, phenylketonuria (PKU), spinal muscular atrophy, paralysis, Wilson disease, epilepsy, Pompe disease, amyotrophic lateral sclerosis (ALS), Tay-Sachs disease, hyperoxaluria 9PH-1), spinocerebellar ataxia type 1 (SCA-1), SCA-3, u-dystrophin, Gaucher's types II or III, arrhythmogenic right ventricular cardiomyopathy (ARVC), Fabry disease, familial Mediterranean fever (FMF), proprionic acidemia, fragile X syndrome, rett syndrome, Niemann-Pick, and Krabbe disease.

All patent and literature references cited in the present specification are hereby incorporated by reference in their entirety.

Clauses

1. An insect cell expressing adeno-associated virus (AAV) VP1 protein and AAV VP3 protein, wherein the insect cell does not express AAV VP2 protein.
2. The insect cell according to clause 1, comprising:
   a. a single nucleotide sequence encoding AAV VP1 protein and AAV VP3 protein; and/or
   b. a first nucleotide sequence encoding AAV VP1 protein and a separate, second nucleotide sequence encoding AAV VP3 protein.
3. The insect cell according to clause 2, wherein the nucleotide sequence defined in (a) comprises:
   a. an open reading frame encoding AAV VP1 protein; and
   b. an open reading frame encoding AAV VP3 protein.
4. The insect cell according to clause 1, comprising a nucleotide sequence encoding adeno-associated virus (AAV) VP2 protein comprising an inactivated VP2 initiation codon.
5. The insect cell according to clause 1, wherein the insect cell further comprises a nucleotide sequence comprising at least one AAV inverted terminal repeat (ITR) nucleotide sequence and at least one nucleotide sequence encoding a gene product of interest.
6. The insect cell according to clause 1, wherein the insect cell further comprises a nucleotide sequence comprising a Rep78 or a Rep68 coding sequence operably linked to expression control sequences for expression in an insect cell.
7. The insect cell according to clause 1, comprising a nucleotide sequence comprising a Rep52 or a Rep40 coding sequence operably linked to expression control sequences for expression in an insect cell.
8. The insect cell according to clause 1, wherein the AAV VP1 protein and the AAV VP3 protein are both encoded by a first nucleic acid construct.
9. The insect cell according to clause 8, wherein the first nucleic acid construct additionally comprises a Rep78 or a Rep68 coding sequence operably linked to expression control sequences for expression in an insect cell.

10. The insect cell according to clause 9, wherein the first nucleic acid construct additionally comprises a Rep52 or a Rep40 coding sequence operably linked to expression control sequences for expression in an insect cell.
11. The insect cell according to clause 9 further comprising a second nucleic acid construct comprising a second nucleotide sequence comprising at least one AAV inverted terminal repeat (ITR) nucleotide sequence and at least one nucleotide sequence encoding a gene product of interest.
12. The insect cell of clause 11, wherein the second nucleic acid construct is an insect cell-compatible vector.
13. The insect cell of clause 12, wherein the insect cell-compatible vector is a baculoviral vector.
14. A nucleic acid construct comprising a nucleotide sequence encoding an adeno-associated virus (AAV) VP1 protein and AAV VP3 protein, wherein the nucleic acid construct does not express AAV VP2 protein, and wherein the nucleic acid sequence is operably linked to expression control sequences for expression in an insect cell.
15. The nucleic acid construct according to clause 14 further comprising a Rep78 or a Rep68 coding sequence operably linked to expression control sequences for expression in an insect cell.
16. The nucleic acid construct according to clause 15 further comprising a Rep52 or a Rep40 coding sequence operably linked to expression control sequences for expression in an insect cell.
17. The nucleic acid construct according to clause 14, wherein the nucleotide sequence encoding the AAV VP1 protein and/or the AAV VP3 protein is codon optimized for expression in an insect cell.
18. A method of increasing the capacity of an AAV gene therapy vector comprising expressing a nucleic acid construct according to clause 14 in an insect cell, thereby increasing the capacity of the AAV gene therapy vector relative to an AAV virion comprising VP1, VP2, and VP3 capsid proteins.
19. A method of increasing the genomic copy titer of an AAV gene therapy vector comprising expressing a nucleic acid construct according to clause 14 in an insect cell, thereby increasing the genomic copy titer of the AAV gene therapy vector relative to an AAV virion comprising VP1, VP2, and VP3 capsid proteins.
20. A nucleic acid construct comprising:
a. a nucleotide sequence which comprises an open reading frame encoding adeno-associated virus (AAV) VP1 protein; and,
b. a nucleotide sequence which comprises an open reading frame encoding AAV VP3 protein; wherein the open reading frames encoding the AAV VP1 protein and the AAV VP3 protein are operably linked to expression control sequences for expression in an insect cell, and wherein AAV VP2 protein is not encoded by the nucleic acid construct.
21. The nucleic acid construct according to clause 20, wherein the open reading frame encoding AAV VP3 protein overlaps with the open reading frame encoding AAV VP1 protein.
22. The nucleic acid construct according to clause 20, wherein the open reading frames encoding the AAV VP1 protein and the AAV VP3 protein are organized such that the AAV VP1 protein and the AAV VP3 protein are transcribed as a single RNA transcript upon expression.
23. The nucleic acid construct according to clause 20, wherein the open reading frame encoding AAV VP3 protein and the open reading frame encoding AAV VP1 protein are transcribed from separate expression cassettes.
24. The nucleic acid construct according to clause 20, wherein the open reading frame encoding AAV VP3 protein and the open reading frame encoding AAV VP1 protein are transcribed from a single expression cassette.
25. A method of increasing the capacity of an AAV gene therapy vector comprising expressing a nucleic acid construct according to clause 20 in an insect cell, thereby increasing the capacity of the AAV gene therapy vector relative to an AAV virion comprising VP1, VP2, and VP3 capsid proteins.
26. A method of increasing the genomic copy titer of an AAV gene therapy vector comprising expressing a nucleic acid construct according to clause 20 in an insect cell, thereby increasing the genomic copy titer of the AAV gene therapy vector relative to an AAV virion comprising VP1, VP2, and VP3 capsid proteins.
27. An AAV virion produced in an insect cell, comprising in its genome:
a. a first nucleic acid sequence encoding at least one gene of interest;
b. a second nucleic acid encoding an AAV VP1 protein, the second nucleic acid being operably linked to an expression control sequence for expressing of AAV VP1 in an insect cell; and
c. a third nucleic acid encoding an AAV VP3 protein, the third nucleic acid being operably linked to an expression control sequence for expressing of AAV VP3 in an insect cell;
wherein the AAV virion comprises a capsid comprising an AAV VP1 protein and an AAV VP3 protein but does not comprise an AAV VP2 protein.
28. The AAV virion according to clause 27, wherein the first nucleotide sequence is positioned between two AAV ITR nucleotide sequences.
29. The AAV virion according to clause 27, wherein the gene of interest is a therapeutic gene.
30. The AAV virion according to clause 29, wherein the therapeutic gene is Factor VIII.
31. The AAV virion according to clause 29, wherein the therapeutic gene is a microRNA, siRNA, or shRNA targeting a disease-causing gene.
32. The AAV virion according to clause 27, wherein the AAV is selected from the group consisting of AAV serotype 1 (AAV1), AAV2, AAV3, AAV4, AAV5, AAV6, AAV7, AAV8, AAV9, AAV10, AAV11, AAV12 and AAV13.
33. The AAV virion according to clause 27, wherein the AAV is AAV1 or AAV5.
34. The AAV virion according to clause 27, wherein the AAV is AAV6, AAV7, AAV8, AAV9, or AAV10.
35. The AAV virion according to clause 27, wherein the AAV is a recombinant AAV (rAAV).
36. The AAV virion according to clause 35, wherein the rAAV is rAAV2/5, wherein the rAAV2/5 comprises at least a portion of AAV2 and AAV5.
37. The AAV virion according to clause 27, wherein the AAV is a chimeric AAV (AAVch).

38. The AAV virion according to clause 37, wherein the AAVch is a chimeric AAV serotype 5 (AAV5ch).
39. The AAV virion according to clause 27, wherein the AAV is a mutant or variant AAV.
40. The AAV virion according to clause 27, wherein the ratio of VP1 protein to VP3 protein is between about 1:5 and about 1:10.
41. The AAV virion according to clause 27, wherein the ratio of VP1 protein to VP3 protein is about 1:5.
42. A pharmaceutical composition comprising the AAV virion according to clause 27.
43. A method for producing recombinant AAV virion in an insect cell comprising:
  a. culturing the insect cell of clause 1 under conditions that permit production of the recombinant AAV virion; and
  b. recovering the recombinant AAV virion from the culture.
44. The method of clause 43, wherein the capacity of the AAV virion is increased relative to an AAV virion comprising VP1, VP2, and VP3 capsid proteins.
45. The method of clause 43, wherein culturing the insect cell of clause 1 under conditions that permit production of the recombinant AAV virion increasing genomic copy titer of the recombinant AAV virion relative to the genomic copy titer achieved by culturing an AAV virion comprising VP1, VP2, and VP3 capsid proteins under the same conditions.
46. The method of clause 43, wherein the ratio of VP1 protein to VP3 protein is between about 1:4 and about 1:59.
47. The method of clause 43, wherein the ratio of VP1 protein to VP3 protein is about 1:5.
48. A method of increasing expression of a gene of interest in a subject, comprising, administering to the subject a therapeutically effective amount of the AAV virion of clause 27, thereby increasing expression of the gene of interest encoded in the AAV virion genome.
49. The method of clause 48, wherein the gene of interest is a therapeutic gene.
50. The method of clause 48, wherein the subject is a human subject.
51. A method of treating a genetic disease in a subject comprising, administering to a subject with a genetic disease a therapeutically effective amount of a recombinant AAV virion, the recombinant AAV virion comprising in its genome a first nucleic acid sequence encoding at least one therapeutic gene; wherein the AAV virion comprises a capsid comprising an AAV VP1 protein and an AAV VP3 protein but does not comprise an AAV VP2 protein.
52. The method of clause 51, is a gene encoding a protein that is mutated or deficient in the genetic disease.
53. The method of clause 51, wherein the therapeutic gene is a microRNA, siRNA, or shRNA targeting a genetic disease-causing gene.
54. The method of clause 51, wherein the genetic disease is a Factor VIII deficiency.
55. The method of clause 52, wherein the at least one therapeutic gene is a Factor VIII gene.
56. The method of clause 51, wherein the genetic disease is a form of hemophilia or a clotting disorder.
57. The method of clause 56, wherein the at least one therapeutic gene is a gene encoding a clotting factor that is deficient or mutated in the clotting disorder.
58. The method of clause 56, wherein the form of hemophilia is hemophilia A or hemophilia B.
59. The method of clause 51, wherein the genetic disease is Huntington's disease.
60. The method of clause 59, wherein the at least one therapeutic gene is a microRNA, siRNA, or shRNA that targets a mutated Huntingtin gene.
61. The method of clause 51, wherein the genetic disease is selected from acute intermittent porphyria (AIP), age-related macular degeneration, Alzheimer's disease, arthritis, Batten disease, Canavan disease, Citrullinemia type 1, Crigler Najjar, congestive heart failure, cystic fibrosis, Duchene muscular dystrophy, dyslipidemia, glycogen storage disease type I (GSD-I), hemophilia A, hemophilia B, hereditary emphysema, homozygous familial hypercholesterolemia (HoFH), Huntington's disease (HD), Leber's congenital amaurosis, methylmalonic academia, ornithine transcarbamylase deficiency (OTC), Parkinson's disease, phenylketonuria (PKU), spinal muscular atrophy, paralysis, Wilson disease, epilepsy, Pompe disease, amyotrophic lateral sclerosis (ALS), Tay-Sachs disease, hyperoxaluria 9PH-1), spinocerebellar ataxia type 1 (SCA-1), SCA-3, u-dystrophin, Gaucher's types II or III, arrhythmogenic right ventricular cardiomyopathy (ARVC), Fabry disease, familial Mediterranean fever (FMF), proprionic acidemia, fragile X syndrome, Rett syndrome, Niemann-Pick, and Krabbe disease.

The following examples are offered for illustrative purposes only, and are not intended to limit the scope of the present invention in any way.

VI. EXAMPLES

Example 1—VP2-Less AAV Viral Vectors Have Increased Capacity

Figure 2:
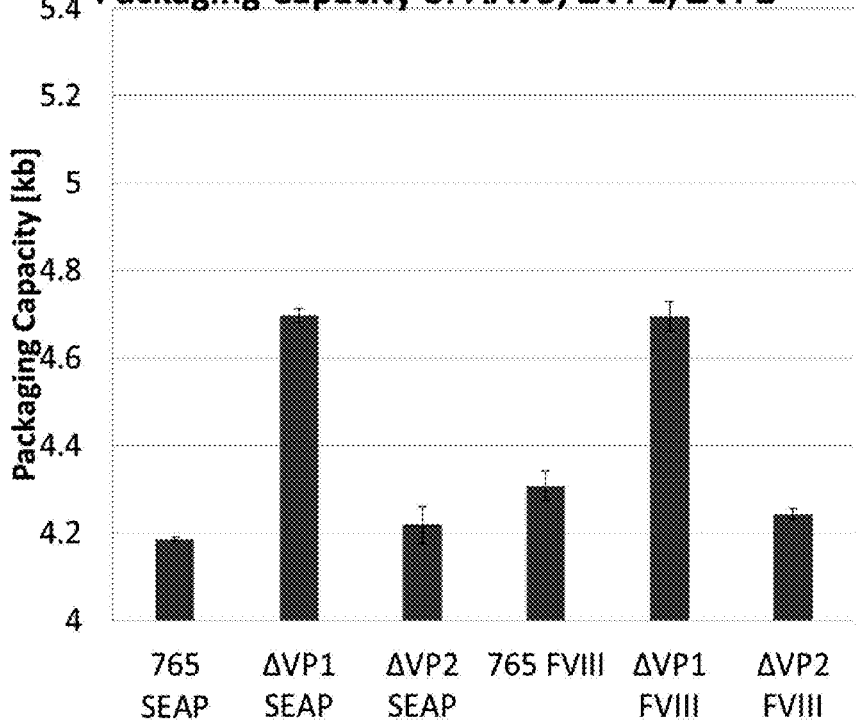
FIG. 2 shows that deleting VP2 does not change packaging capacity compared to wild type AAV5 (AAV 765) when secreted alkaline phosphatase (SEAP; 2.8 kB) is the transgene that is used.
Figure 5:
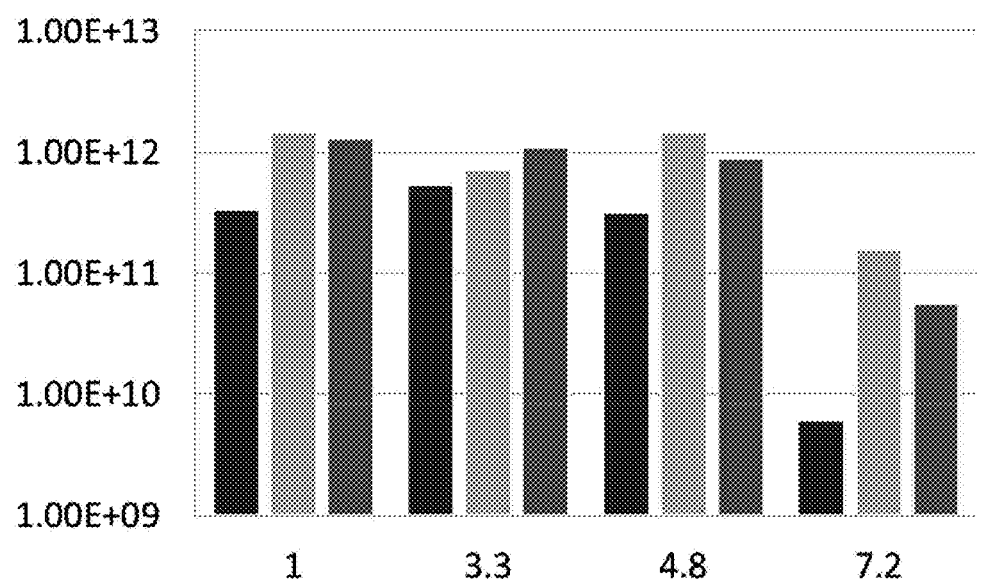
FIG. 5 shows that ΔVP1 and ΔVP2 have higher production efficiency than 765. Difference more significant if transgene exceeds capacity limit. Titer of isolated AAV of 765, ΔVP1, ΔVP2 with microRNA (1 kb, 3.3 kb, 4.8 kb) and FVIII (7.2 kB) is shown.

Packaging capacity was compared by inserting transgenes of varying sizes into VP2 deleted AAV5 viral vectors, VP1 deleted AAV5 vectors, and AAV5 vectors containing VP1, VP2, and VP3. Vector production was performed as previously described (WO2015/137802), the 765 vector was modified to have either the VP2 or the VP1 initiation codon inactivated and vector production was compared with the unmodified 765 vector. The transgenes used were sizes: 1 kB, 3.3 kB, 4.8 kB, which encoded a miRNA, and Factor VIII with a size of 7.2 kB. FIG. 1 shows that VP1 deletion increases the capacity to carry larger gene inserts, whereas deleting VP2 does not increase the capacity to package larger genes. Changing the transgene to the smaller SEAP transgene (2.8 kB) does not increase the VP2-less AAV's capacity compared to the AAV with VP1, VP2, and VP3. FIG. 2. However, the formaldehyde gels in FIG. 3 and FIG. 4 reveals that the VP2-less vectors can produce virions that package larger amount of transgenes. Formaldehyde gels were made by subjecting (purified) recombinant AAV vector to a DNase treatment, followed subsequently by isolating DNA from the capsids by protease treatment. DNA was then bound to a spin column and eluted and loaded on a formaldehyde gel. The formaldehyde gel is ideal for visualizing single stranded DNA and have good granularity of the size. Looking at the titer (FIG. 5) and the comparable gel (FIG. 3) you see that VP2 deletion gives higher titers and, for equivalent volume, larger DNA amounts (FIG. 3). Also, the next figure (FIG. 4) which is an overexposure of FIG. 3 shows that the VP2 deletion can also package the higher sized DNA observed with the VP1 deletion, but at much lower amounts, whereas 765 cannot package that size at all as can be seen from the overexposed gel (FIG. 4).

Example 2—VP2-Less AAV Have Higher Production Efficiency Than Wild Type

Production efficiency, i.e. genomic copy titer, of wild type AAV5, VP1 deleted AAV5, and VP2 deleted AAV5 with inserts of sizes: 1 kB, 3.3 kB, 4.8 kB, encoding a microRNA, or Factor VIII with a size of 7.2 kB. For the inserts up to 4.8 kB, the production efficiency was the same for the wild type AAV5, VP1 deleted AAV5, and VP2 deleted AAV5. See FIG. 5. However, for the 7.2 kB sized Factor VIII insert, VP1 less and VP2-less AAV had increased genomic copy titer relative to wild type like capsids. The genome copy titer was measured by qPCR of a DNAse protected fragment. The DNA inside the capsid is protected from DNAse and is therefore efficiently quantified from any contaminating DNA floating around. A higher titer and genomic copy number indicates more virus formed. From FIG. 5 it can be seen that the bigger the inserted DNA is the easier it is for the VP1 deletion and VP2 deletion to produce an acceptable titer and is much more successful than normal AAV. Overall titers for VP2 deletion are higher than wtAAV comprising VP1, VP2 and VP3.

Example 3—VP2-Less AAV Remains Infectious

To compare infectious potency between wild type AAV5, VP1 deleted AAV5, and VP2 deleted AAV5, a SEAP assay was performed in Huh7 cells. See FIG. 6. The assay showed that VP2-less AAV had the same or very similar potency as wild type AAV5; whereas, VP1 less AAV completely lost infectivity. AAV vector produced was added in 3 different genome copy concentrations to Huh7 cells and the expression of SEAP as transgene is measured with a commercially available kit (Roche) wherein a substrate is converted into a fluorescent end product by the SEAP (alkaline phosphatase).

The invention claimed is:

1. An insect cell expressing adeno-associated virus (AAV) VP1 protein and AAV VP3 protein and not expressing AAV VP2 protein, wherein the insect cell comprises an exogenous nucleotide sequence of 6.1 kb of at least one gene of interest.

2. The insect cell according to claim 1, comprising:
(a) a nucleotide sequence encoding AAV VP1 protein and AAV VP3 protein; and/or
(b) a nucleotide sequence encoding AAV VP1 protein and a nucleotide sequence encoding AAV VP3 protein.

3. The insect cell according to claim 2, wherein the nucleotide sequence as defined in (a) of claim 2 comprises:
(a) an open reading frame encoding AAV VP1 protein; and
(b) an open reading frame encoding AAV VP3 protein.

4. The insect cell according to claim 1, comprising a nucleotide sequence encoding adeno-associated virus (AAV) VP2 protein with an inactivated VP2 initiation codon.

5. The insect cell according to claim 1, wherein the insect cell further comprises: (i) a nucleotide sequence comprising a Rep78 or a Rep68 coding sequence operably linked to expression control sequences for expression in an insect cell; and optionally, (ii) a nucleotide sequence comprising a Rep52 or a Rep40 coding sequence operably linked to expression control sequences for expression in an insect cell.

6. The insect cell according to claim 5, wherein the insect cell comprises: (a) a first nucleic acid construct comprising (i) nucleotide sequences for AAV VP1 protein and AAV VP3 protein, (ii) the nucleotide sequence comprising a Rep78 or a Rep68 coding sequence and, optionally, (iii) the nucleotide sequence comprising a Rep52 or a Rep40 coding sequence; and, (b) a second nucleic acid construct comprising an exogenous nucleotide sequence of at least 6.1 kb of at least one gene of interest.

7. The insect cell according to claim 6, wherein the second nucleic acid construct is an insect cell-compatible vector.

8. The insect cell according to claim 7, wherein the vector is a baculoviral vector.

9. A method for producing an AAV in an insect cell, comprising:
(a) culturing an insect cell according to claim 5 under conditions to produce AAV; and optionally,
(b) recovering the AAV.

10. An AAV virion produced in an insect cell according to claim 1, the AAV virion comprising in its genome at least one nucleotide sequence encoding a gene product of interest, wherein the at least one nucleotide sequence is not a native AAV nucleotide sequence, and wherein the AAV virion comprises AAV VP1 protein and AAV VP3 protein and does not comprise AAV VP2 protein.

11. The AAV virion according to claim 10, wherein the at least one nucleotide sequence encoding a gene product of interest is located between two AAV ITR nucleotide sequences.

12. A pharmaceutical composition, comprising the AAV virion according to claim 10.

* * * * *